(12) United States Patent
Kim et al.

(10) Patent No.: US 11,877,852 B2
(45) Date of Patent: Jan. 23, 2024

(54) APPARATUS AND METHOD FOR CLASSIFYING STRESS

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Kyeung Ho Kang, Gwangju (KR); Si Ho Shin, Gwangju (KR); Min Gu Kang, Suncheon-si (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 181 days.

(21) Appl. No.: 17/527,695

(22) Filed: Nov. 16, 2021

(65) Prior Publication Data

US 2022/0183605 A1    Jun. 16, 2022

(30) Foreign Application Priority Data

Nov. 19, 2020   (KR) .................. 10-2020-0155959

(51) Int. Cl.
*A61B 5/329* (2021.01)
*A61B 5/352* (2021.01)
(Continued)

(52) U.S. Cl.
CPC .............. *A61B 5/329* (2021.01); *A61B 5/352* (2021.01); *A61B 5/7203* (2013.01);
(Continued)

(58) Field of Classification Search
CPC ....... A61B 5/329; A61B 5/352; A61B 5/7203; A61B 5/7267; G06F 18/23213; G06N 3/04
See application file for complete search history.

(56) References Cited

U.S. PATENT DOCUMENTS

2016/0089038 A1* 3/2016 Chadderdon, III ........................ A61B 5/02055 600/301
2017/0127993 A1* 5/2017 Olivier ............... A61B 5/02055
(Continued)

FOREIGN PATENT DOCUMENTS

KR    10-2008-0038512 A    5/2008

OTHER PUBLICATIONS

Mingu Kang, et.al, "Stress Classification Using K-means Clustering and Heart Rate Variability from Electrocardiogram", 4th European Conference on Electrical Engineering & Computer Science, EECS 2020: Bern, Switzerland, Dec. 21-22, 2020.
(Continued)

*Primary Examiner* — Catherine M Voorhees
*Assistant Examiner* — Roland Dinga
(74) *Attorney, Agent, or Firm* — Renner, Otto, Boisselle & Sklar, LLP

(57) ABSTRACT

An apparatus for classifying stress includes an electrocardiogram (ECG) measurement module configured to measure an ECG signal in a first state, an idle state, and an ECG signal in a second state in which noise, having various magnitudes, is generated, a feature point extraction module configured to extract a feature point of each of the measured ECG signal in the first state and the measured ECG signal in the second state, and a clustering module configured to perform K-means clustering on the ECG signals in the first and second states based on the extracted feature points to classify stress.

12 Claims, 6 Drawing Sheets

(51) Int. Cl.
    *G06N 3/04*         (2023.01)
    *A61B 5/00*         (2006.01)
    *G06F 18/23213*     (2023.01)

(52) U.S. Cl.
    CPC ...... *A61B 5/7267* (2013.01); *G06F 18/23213* (2023.01); *G06N 3/04* (2013.01); *G06F 2218/12* (2023.01)

(56) References Cited

U.S. PATENT DOCUMENTS

| | | | |
|---|---|---|---|
| 2018/0249939 A1* | 9/2018 | Huang | A61B 5/165 |
| 2020/0012665 A1* | 1/2020 | Das | G06F 18/2113 |
| 2020/0187807 A1* | 6/2020 | Trigueiros Da Silva Cunha | A61B 5/316 |

OTHER PUBLICATIONS

Korean Office Action issued for corresponding KR Application No. 10-2020-0155959, dated Nov. 24, 2021.
L. Medina, "Identification of stress states from ECG signals using unsupervised learning methods," Apr. 2009, p. 1-13.
S. Ye, et al., "Evaluation on the stress using HRV according to elapsed time of MRI noise," Busan Catholic University, Journal of Signal Processing Systems, vol. 16, No. 2, Apr. 2015, p. 50-55.
M. N. Rastgoo, "Driver stress level detection based on multimodal measurements," PhD. Thesis of school of electrical engineering and computer science, science and Engineering faculty queensland university of technology, p. i-xv, pp. 1-182 (2019).

\* cited by examiner

APPARATUS AND METHOD FOR CLASSIFYING STRESS

CROSS-REFERENCE TO RELATED APPLICATION(S)

The present application claims the benefit of priority to Korean Patent Application No. 10-2020-0155959, filed on Nov. 19, 2020 in the Korean Intellectual Property Office, the entire disclosure of which is incorporated herein by reference.

BACKGROUND

1. Field

The present disclosure relates to an apparatus and a method for classifying stress.

2. Description of Related Art

Modern people in the 21st century are living in an environment which is subject to various stressful factors such as concerns about human relationships, workload, and economic anxiety in a constantly changing society. Stress refers to a state of psychological and physical tension experienced in an environment which may be difficult to adapt to. When a person is excited or tense, an autonomic nervous system may be activated and a numerical value of a frequency band corresponding to the autonomic nervous system may be increased. Meanwhile, in a relaxed or psychologically stable state, a numerical value of a frequency band of a parasympathetic nervous system may be increased. When a person is stressed, a frequency of an LF (0.04 to 0.15 Hz) band may be increased 3.3 times that of an HF (0.15 to 0.5 Hz) band.

Currently, many methods for measuring stress are being researched. An example of the methods is a method of analyzing stress using noise of magnetic resonance imaging (MRI). However, research into an effect of noise on the human body requires require long-term data collection and has difficulty in directly confirming the effect of noise on the human body.

In addition, a stress analysis method using a Pan-Tompkins technique, detecting an R-peak of an electrocardiogram (ECG), takes significantly a large amount of time to calculate an R-R interval and exhibits relatively low stress analysis accuracy of 49.6%.

In addition, a stress analysis method using a brainwave takes a large amount of time and has difficulty in accurately distinguishing a stressed person and a non-stressed person from each other because the amount of data may be too small.

In addition, a method for obtaining a long-term electrocardiogram (ECG) and analyzing stress requires a large amount of time to measure a stress signal and has difficulty in determining a stress state because a stress index is not accurately presented. Since a conventional ECG classification algorithm using a convolution neural network (CNN) includes 34 multiple layers and classification time is significantly long, classification accuracy is as low as 88.1%.

SUMMARY

An aspect of the present disclosure is to provide an apparatus and a method for classifying stress which may allow a stress index to be relatively easily checked to help mental health management of modern people suffering from stress and to prevent various diseases such as depression, hypertension, and diabetes.

According to an aspect of the present disclosure, an apparatus for classifying stress includes an electrocardiogram (ECG) measurement module configured to measure an ECG signal in a first state, an idle state, and an ECG signal in a second state in which noise, having various magnitudes, is generated, a feature point extraction module configured to extract a feature point of each of the measured ECG signal in the first state and the measured ECG signal in the second state, and a clustering module configured to perform K-means clustering on the ECG signals in the first and second states based on the extracted feature points to classify stress.

According to an aspect of the present disclosure, a method of classifying stress includes measuring an electrocardiogram (ECG) signal in a first state, an idle state, and an ECG signal in a second state, in which noise, having various magnitudes, is generated, by an ECG measurement module, extracting a feature point of each of the measured ECG module in the first state and the measured ECG module in the second state by a feature point extraction module, and performing K-means clustering on the ECG signals in the first state and the second state based on the extracted feature points to classify stress by a clustering module. The extracted feature points include an R-peak value and an S-peak point of an ECG signal.

BRIEF DESCRIPTION OF DRAWINGS

The above and other aspects, features, and advantages of the present disclosure will be more clearly understood from the following detailed description, taken in conjunction with the accompanying drawings.

DETAILED DESCRIPTION

Figure 1:
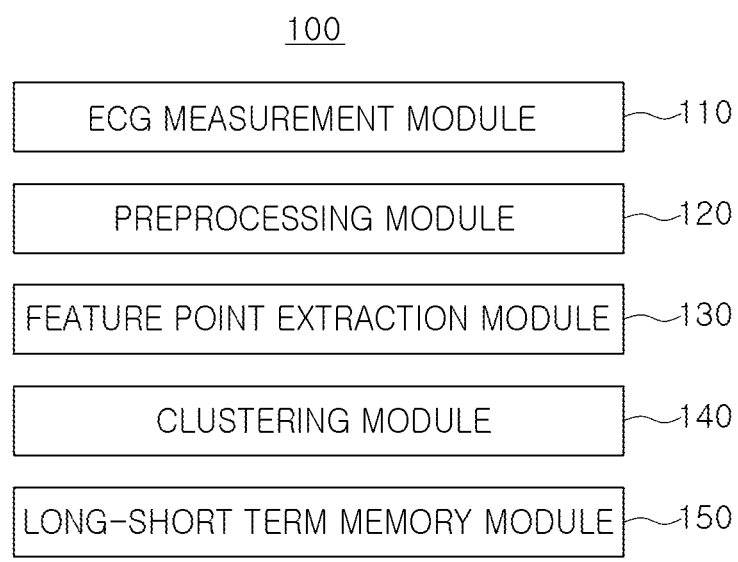
FIG. 1 is a block diagram of an apparatus for classifying stress according to an example embodiment of the present disclosure.

Hereinafter, example embodiments of the present disclosure will be described in detail with reference to the accompanying drawings. The present disclosure may, however, be embodied in many different forms, and should not be construed as being limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

FIG. 1 is a block diagram of an apparatus 100 for classifying stress according to an example embodiment.

As illustrated in FIG. 1, the apparatus 100 for classifying stress according to an example embodiment may include an electrocardiogram (ECG) measurement module 110, a preprocessing module 120, a feature point extraction module 130, a clustering module 140, and a long-short term memory network module 150.

Specifically, the ECG measurement module 120 may be a device measuring an ECG of a subject, and may measure an ECG signal in a first state, in which the ECG signal is idle, and an ECG signal in a second state, in which noise of various magnitudes (for example, 10 dB, 20 dB, 30 dB, 40 dB, 50 dB, 60 dB, 70 dB, 80 dB, 90 dB, and the like) occurs, and may transmit the measured ECG signal in the first state and the measured ECG signal in the second state to the preprocessing module 120.

The preprocessing module 120 may be provided to preprocess an ECG signal measured by the ECG measurement module 110, and may be a module canceling noise from the measured ECG signal. The ECG signal, from which noise has been canceled by the preprocessing module 120, may be transmitted to the feature point extraction module 130. The preprocessing module 120 may include, for example, a median filter and a low-pass filter.

The feature point extraction module 130 may extract a feature point of each of the measured ECG signal in the first state and the measured ECG signal in the second state. The feature points may include an R-peak value and an S-peak value of an ECG signal.

For example, the feature point extraction module 130 may set a threshold value. When the ECG signal exceeds the set threshold value, the feature point extraction module 130 may set a value at that point in time to an R-peak value or an S-peak value.

Figure 2A:
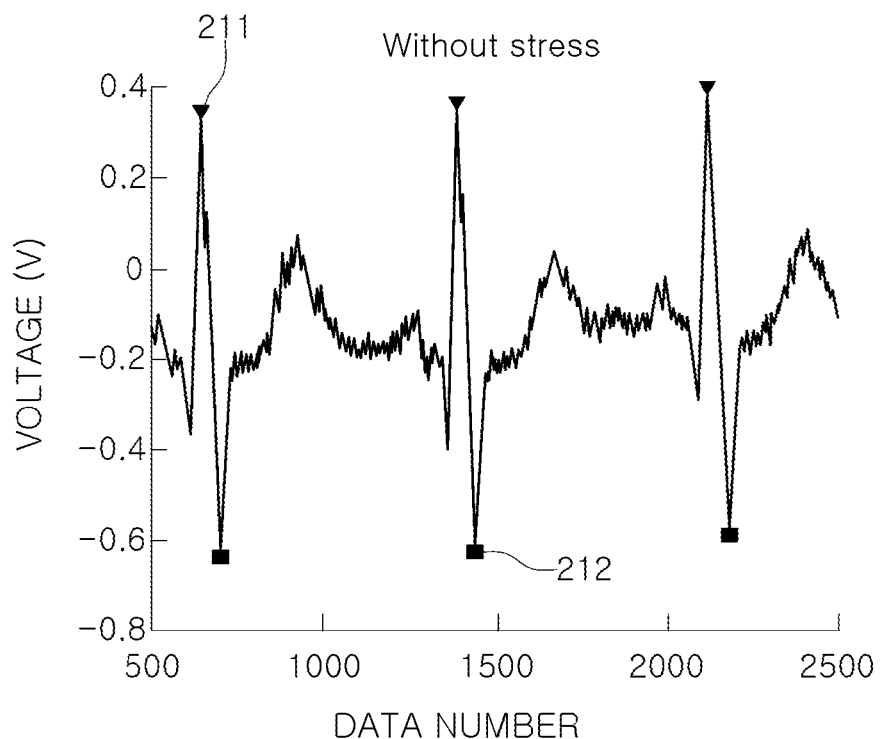
FIG. 2A and FIG. 2B illustrate a comparison between a first state ("without state") and a second state ("under stress") measured according to an example embodiment of the present disclosure.
Figure 2B:
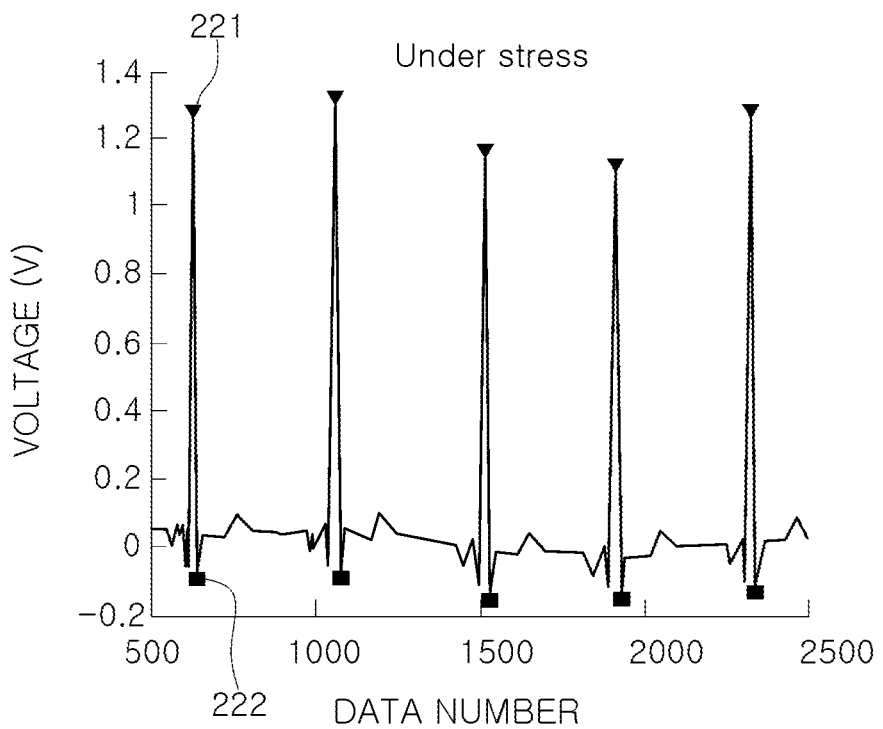

In this regard, FIG. 2A and FIG. 2B illustrate a comparison between a first state ("without stress") and a second state ("under stress") measured according to an example embodiment. FIG. 2A illustrates the first state and FIG. 2B illustrates the second state. In FIG. 2A and FIG. 2B, a reference numeral 211 represents an R-peak value in the first state, a reference numeral 212 represents an S-peak value in the first state, a reference numeral 221 represents an R-peak value in the second state, and a reference numeral 222 represents an S-peak value in the second state.

Referring to FIG. 2A and FIG. 2B, it can be seen in FIG. 2A that in the case of an ECG signal of a subject exposed to noise, a heart rate is increased, an interval of the ECG signal is formed to irregular, and an R-peak value and an S-peak value are great. Meanwhile, it can be seen in FIG. 2B that in the case of an ECG signal of the subject in an idle state, a heart rate is stable, an interval of the ECG signal is formed to be regular, and an R-peak value and an S-peak value are great.

In the following Table 1, the ECG signal in the first state (the ECG signal in the idle state) and the ECG signal in the second state (the ECG signal exposed to noise) are compared and listed.

TABLE 1

|  | ECG Signal in Idle State | ECG Signal Exposed to Noise |
|---|---|---|
| R-Peak Value (mV) | 0.38 | 1.36 |
| S-Peak Value (mV) | −0.57 | −0.07 |
| R-S Amplitude Difference (mV) | 0.95 | 1.43 |

Figure 3A:
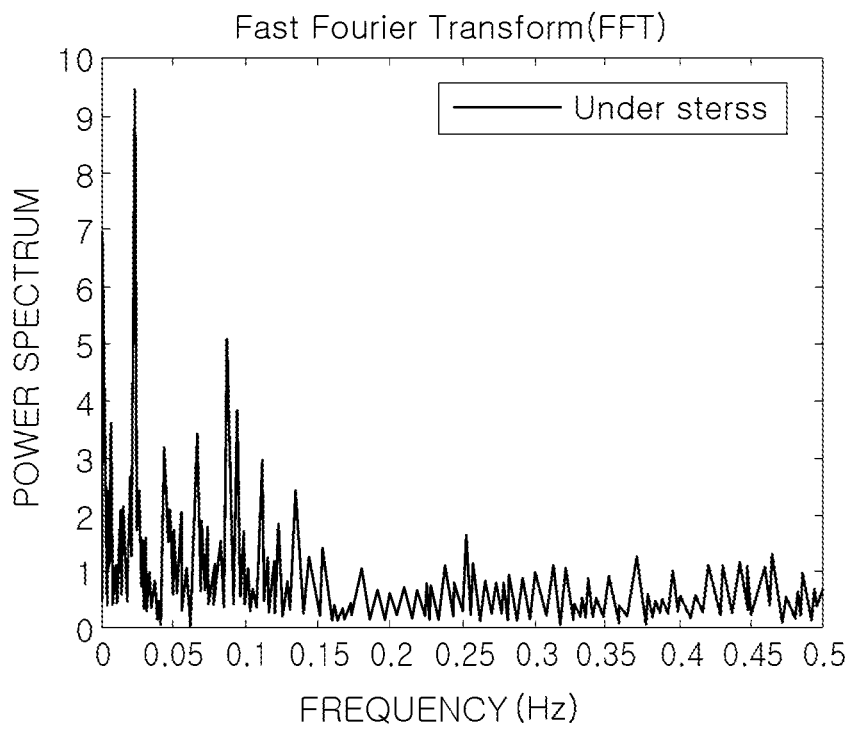
FIG. 3A and FIG. 3B illustrate power spectra for the first state and the second state according to an example embodiment of the present disclosure.
Figure 3B:
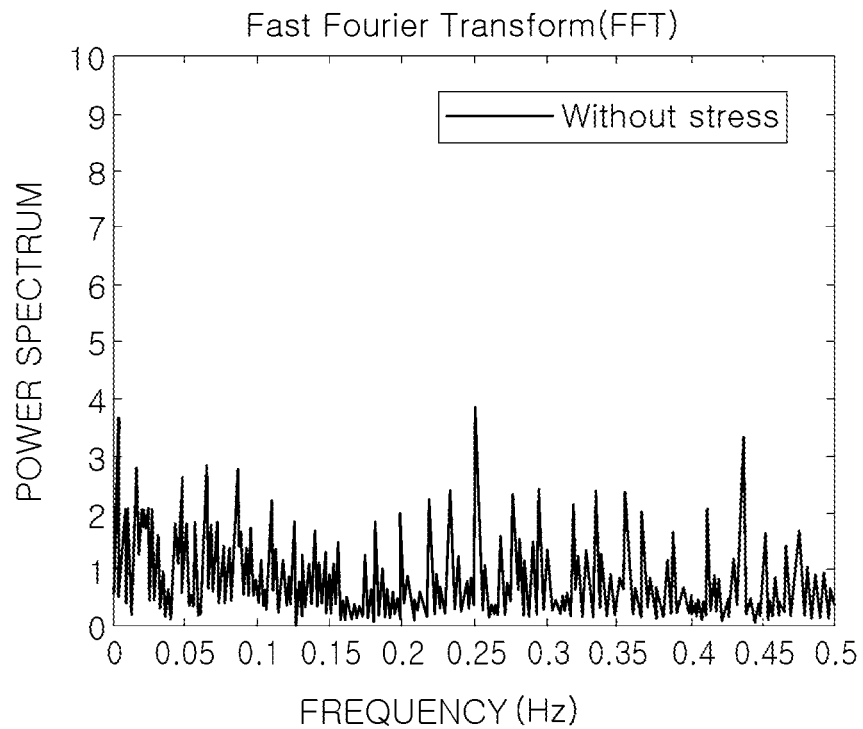

FIG. 3A and FIG. 3B illustrate power spectra of a frequency domain for the first state and the second state according to an example embodiment. FIG. 3A illustrates a power spectrum in the first state, and FIG. 3B illustrates a power spectrum in the second state.

A frequency domain may be divided into three domains, for example, a very Low frequency (VLF) domain (0.003 to 0.04 Hz), a low frequency (LF) domain (0.04 to 0.15 Hz), and a high frequency (HF) domain (0.15 to 0.5 Hz). In an LF band, sympathetic activity may occur, so that a heart rate of a person may be rapidly increased to cause the person to be stressed. In the HF band, parasympathetic activity may occur, so that a heart rate of the person may be decreased to cause the person to be stabilized.

A stress index may be obtained from the above-described power spectrum according to Equation 1, as follow:

$$SI = \frac{LF(ms^2)}{HF(ms^2)} \quad \text{[Equation 1]}$$

where SI may be a stress index, $LF(ms^2)$ may be a low-frequency component, and $HF(ms^2)$ may be a high-frequency component. The low-frequency component may be a component between approximately 0.04 to 0.15 Hz, and the high-frequency component may be a component between approximately 0.15 to 0.4 Hz.

The clustering module 140 may perform k-means clustering on the ECG signals in the first state and the second state, based on the extracted feature points.

Specifically, the clustering module 140 may obtain an R-S amplitude difference, a difference between the R-peak value and the S-peak value, and may express the ECG signals in the first state and the second state as stress levels compared with the R-S amplitude difference, based on a predetermined stress signal classification criteria.

According to the predetermined stress signal classification criteria, a state in which the R-S amplitude difference is 1.2 or more may be the second state and a state in which the R-S amplitude difference is less than 1.2 may be the first state.

More specifically, the predetermined stress signal classification criteria may conform to the following Table 2.

TABLE 2

| ECG Signal | RS Amplitude Difference (mV) | Stress Level |
|---|---|---|
| ECG Signal in Idle State | 0.59 or less | 1 |
|  | 0.6-0.79 | 2 |
|  | 0.8-0.99 | 3 |
|  | 1-1.19 | 4 |
| ECG Signal Exposed to Noise | 1.2-1.39 | 5 |
|  | 1.4-1.59 | 6 |
|  | 1.6-1.79 | 7 |
|  | 1.8 or more | 8 |

The above-mentioned K-means clustering algorithm is a type of clustering model of unsupervised learning. For the K-means clustering, "cluster" refers to a group of datasets having similar characteristics, referring to locations close to each other, "K" refers to the number of clusters, and "means" refers to a centroid of data of a cluster.

For example, "K-means clustering" refer to generating K clusters based on K centroids. In the present disclosure, K was set to 2.

Such a K-means clustering algorithm is aimed at finding an $S_i$ value, minimizing an overall variance, when a center of an i-th cluster is $\mu_i$ and a set of points belonging to a cluster is $S_i$.

Figure 4A:
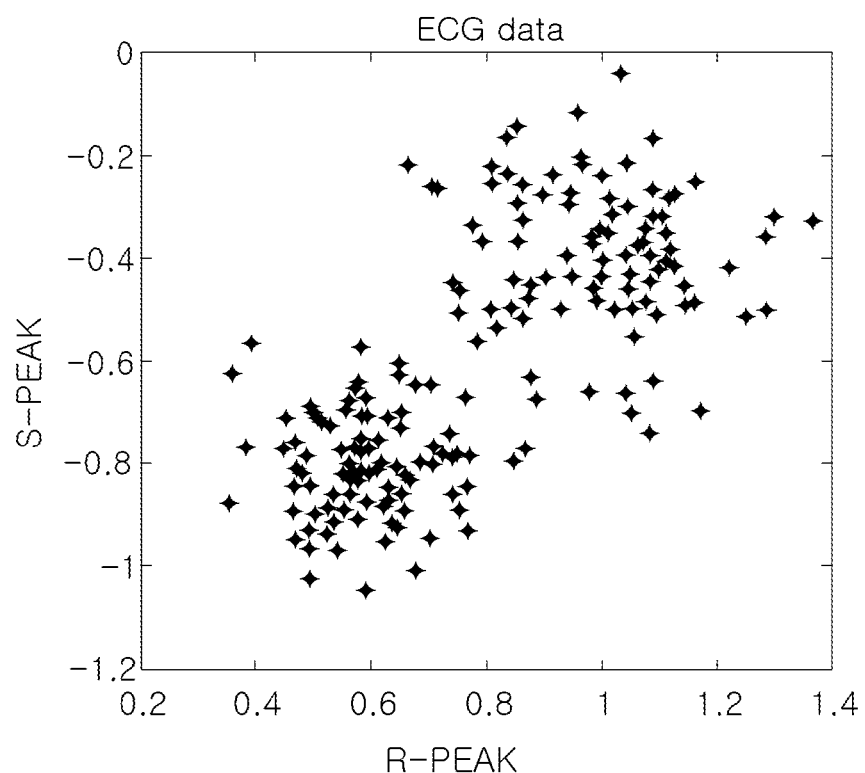
FIG. 4A and FIG. 4B illustrate a K-means clustered electrocardiogram (ECG) signal according to an example embodiment of the present disclosure.
Figure 4B:
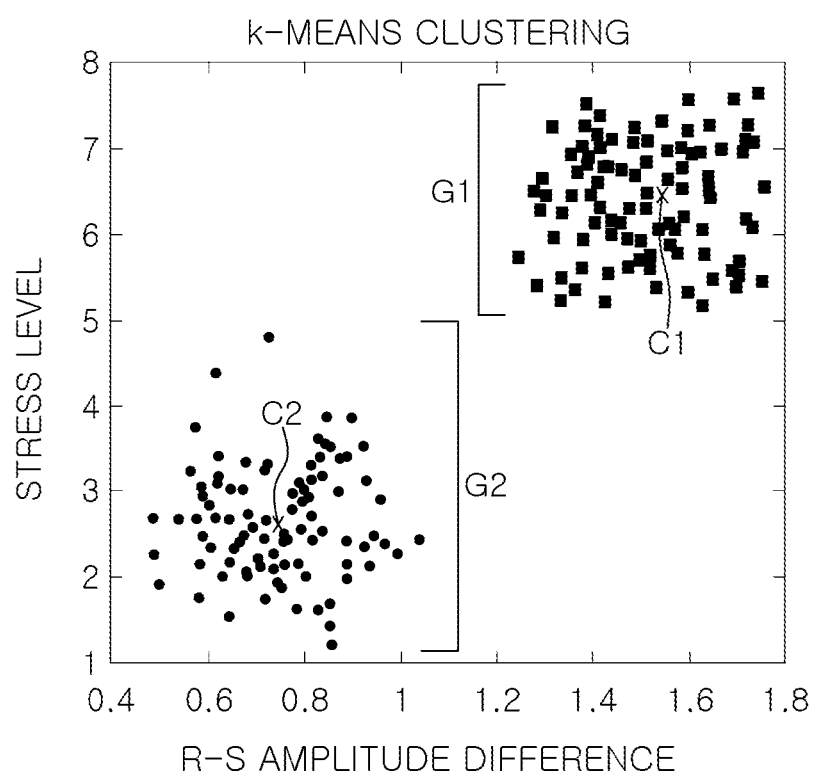

An ECG signal, clustered using the above-described K-means clustering, is illustrated in FIG. 4A and FIG. 4B. FIG. 4A illustrates an R-peak and an S-peak of an ECG signal, and FIG. 4B expresses ECG signals in the first state and the second state as stress levels compared with an R-S amplitude difference, based on predetermined stress signal classification criteria.

As illustrated in FIG. 4B, a mean value may be readjusted based on center points C1 and C2 of K clusters (K=2 in the present disclosure), G1 may be a cluster in the first state, and G2 may be a cluster in the second state.

According to an example embodiment, the long-short term memory module 150 may classify stress in the first state or the second state from the R-peak value and the S-peak value through training using a long-short term memory.

The above-described long-short term memory is a type of recurrent neural network (RNN), and may be an artificial neural network recognizing patterns in data having an array such as text, gene signal analysis, and the like. In a general artificial neural network, when data is input, an operation may be performed sequentially from an input layer through a hidden layer to be output. In this process, input data passes through every node only once. Previous data may not be well memorized.

Unlike a general artificial neural network, RNNs may be connected in such a manner that a result of a hidden layer enters an input terminal of the same hidden layer, which means that an output of a hidden layer is repeatedly input to the same hidden layer. However, since the RNN does not process high-capacity data well, an operation speed may be significantly low. To address such an issue, a long-short term memory (LSTM) may be used. The long-short term memory is a special type of RNN, and may be a neural network designed to perform memorization and training well even when a distance between sequentially input datasets is long.

Figure 5A:
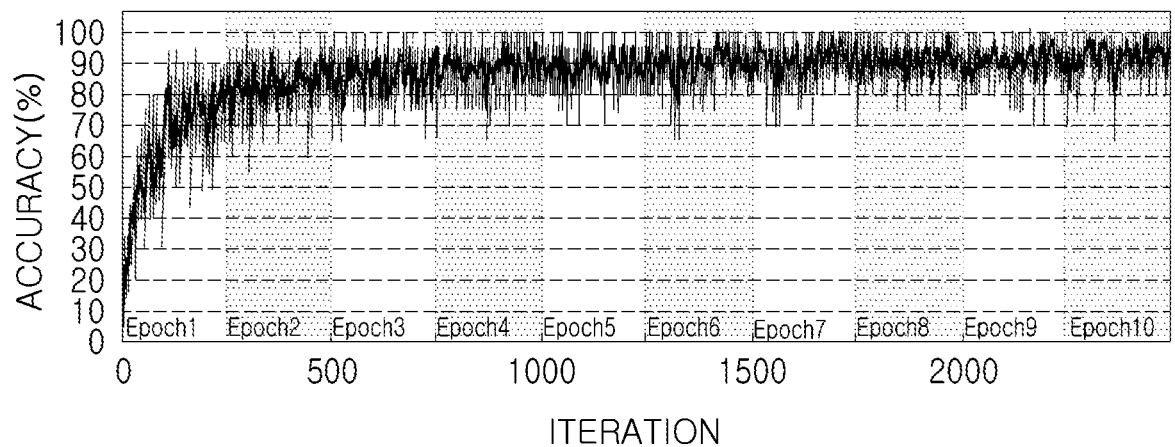
FIG. 5A and FIG. 5B illustrate classification accuracy based on training by a long-short term memory module according to an example embodiment of the present disclosure.
Figure 5B:
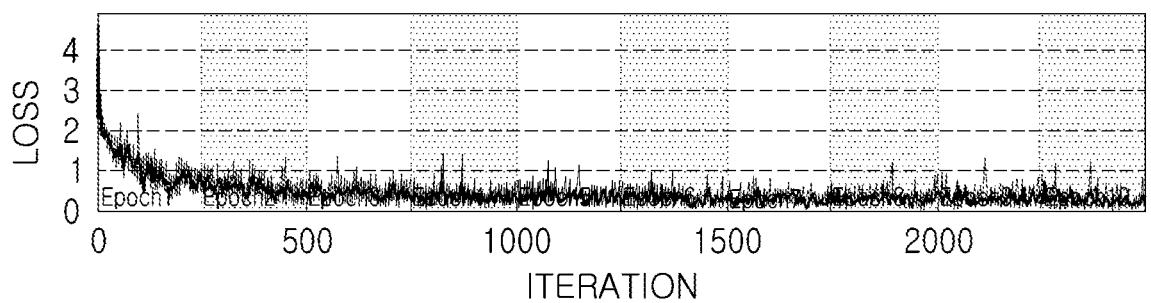

FIG. 5A and FIG. 5B illustrate classification accuracy based on training by a long-short term memory module according to an example embodiment. In FIG. 5A and FIG. 5B, "epoch" means that an overall data set is subject to forward and reverse processes in an artificial neural network. For example, "epoch" means that training for an entire dataset is completed once. "batch size" refers to a data sample size given for each batch, "batch" refers to a divided dataset, and "iteration" refers to the number of times an epoch is divided and executed.

In most cases, entire data cannot be input to a memory in one epoch due to a limitation and a speed reduction of the memory. Therefore, the data is divided. In this case, the number of times the data is divided may be defined as iteration, and a size of data provided for each iteration may be referred to as a batch size.

As illustrated in FIG. 5A, a subplot of a training progress plot represents training accuracy, for example, classification accuracy of each mini-batch. When training is successfully performed, such a value may be usually increased toward 100%. Training loss is represented in a subplot as illustrated in FIG. 5B. When training is successfully performed, such a value may be usually decreased toward 0, and it can be seen that classification accuracy of a signal in an idle state and a signal exposed to noise, obtained using a long-short term memory according to an example embodiment, is 91.45%.

As described above, according to an example embodiment, an ECG signal in a first state, an idle state, and an ECG signal in a second state, in which noises having various magnitudes are generated are measured, may be measured. The measured ECG signal in the first state and the measured ECG signal in the second state may be subjected to K-means clustering, based on a feature point of each of the measured first and second ECG signals, so that a stress index may be easily checked to be helpful in managing mental health of modern people suffering from stress and to be advantageous for preventing various diseases such as depression, hypertension, and diabetes.

Figure 6:
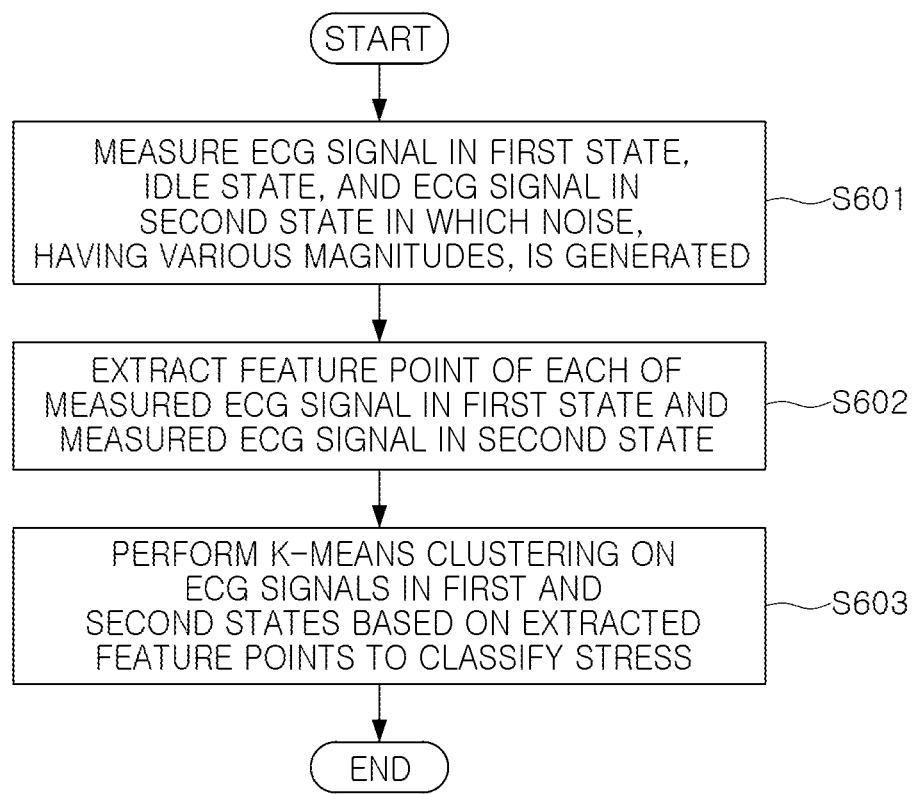
FIG. 6 is a flowchart illustrating a method for classification stress according to an example embodiment of the present disclosure.

FIG. 6 is a flowchart illustrating a method for classification stress according to an example embodiment.

Hereinafter, a method for classifying stress according to an example embodiment will be described in detail with reference to FIGS. 1 to 6. However, duplicate descriptions as those provided above with reference to FIGS. 1 to 5 will be omitted for clarity of the present disclosure.

The method for classifying stress according to an example embodiment may start with operation S601 in which the ECG measurement module 120 measures an ECG signal in a first state, an idle state, and an ECG signal in a second state in which noises having various magnitudes (for example, 10 dB, 20 dB, 30 dB, 40 dB, 50 dB, 60 dB, 70 dB, 80 dB, 90 dB, and the like) are being generated.

The preprocessing module 120 may be provided to preprocess an ECG signal measured by the ECG measurement module 110, and may be a module canceling noise from the measured ECG signal. The ECG signal, from which noise has been canceled by the preprocessing module 120, may be transmitted to the feature point extraction module 130. The preprocessing module 120 may include, for example, a median filter and a low-pass filter.

In operation S602, the feature point extraction module 130 may extract a feature point of each of the measured ECG signal in the first state and the measured ECG signal in the second state. As described above, the feature points may include an R-peak value and an S-peak value of the ECG signals.

In operation S603, the clustering module 140 may perform K-means clustering on the ECG signals in the first state and the second state, based on the extracted feature points.

As described above, the clustering module 140 may obtains an R-S amplitude difference, a difference between the R-peak value and the S-peak value, and may express the ECG signals in the first state and the second state as stress levels compared with the R-S amplitude difference, based on a predetermined stress signal classification criteria.

As described above, according to an example embodiment, an ECG signal in a first state, an idle state, and an ECG signal in a second state, in which noises having various magnitudes are generated are measured, may be measured. The measured ECG signal in the first state and the measured ECG signal in the second state may be subjected to K-means clustering, based on a feature point of each of the measured first and second ECG signals, so that a stress index may be easily checked to be helpful in managing mental health of modern people suffering from stress and to be advantageous for preventing various diseases such as depression, hypertension, and diabetes.

The above-described stress measurement method using an electrocardiogram signal, depending on an influence of noise, according to an example embodiment of the present disclosure may be manufactured as a program to be executed in a computer and stored in a computer-readable recording medium. Examples of computer-readable recording media may include a read-only memory (ROM), a random access memory (RAM), a compact disc ROM (CD-ROM), a magnetic tape, a floppy disk, an optical data storage device, and the like. In addition, the computer-readable recording medium may be distributed over a computer system connected through a network, so that computer-readable codes may be stored and executed in a distributed manner. Functional programs, codes, and code segments for implementing the method may be easily inferred by programmers in the art to which the present disclosure pertains.

In addition, in description of the present disclosure, '~module' may be implemented by various methods, for example, a processor, program commands executed by the processor, a software module, a microcode, a computer program product, a logic circuit, an application-specific integrated circuit, a firmware, and the like.

As described above, according to an example embodiment, an ECG signal in a first state, an idle state, and an ECG signal in a second state, in which noises having various magnitudes are generated are measured, may be measured. The measured ECG signal in the first state and the measured ECG signal in the second state may be subjected to K-means clustering, based on a feature point of each of the measured first and second ECG signals, so that a stress index may be easily checked to be helpful in managing mental health of modern people suffering from stress and to be advantageous for preventing various diseases such as depression, hypertension, and diabetes.

While exemplary embodiments have been shown and described above, it will be apparent to those skilled in the art that modifications and variations could be made without departing from the scope of the present disclosure as defined by the appended claims.

What is claimed is:

1. A computer system for classifying electrical signals representing stress experienced by a subject, computer system comprising:
one or more computer processors configured to:
measure one or more instances of an electrocardiogram (ECG) signal categorized in sequentially input datasets, each ECG signal being in either a first state in which the ECG signal is idle or a second state in which noise is generated;
extract one or more feature points of each measured ECG signal in the first state and in the second state, wherein extracted feature points comprise an R-peak value and an S-peak value of a respective ECG signal;
perform K-means clustering on the ECG signals in the first and second states based on extracted feature points and generate clustered ECG signals based on performed K-means clustering; and
classify stress experienced by the subject in the first state or the second state based on an R-peak value and an S-peak value calculated based on clustered ECG signals and train a long-short term memory (LTSM), a type of recurrent neural network (RNN), to recognize patterns in clustered ECG signals even when a distance between sequentially input datasets is relatively long.

2. The computer system of claim 1, wherein one or more computer processors are further configured to:
determine an R-S amplitude difference value based on classification of stress in the first state or the second state, wherein:
the R-S amplitude difference value is indicative of a difference between the R-peak value and the S-peak value and expresses ECG as stress levels compared with the R-S amplitude difference value.

3. The computer system of claim 2, wherein one or more computer processors are further configured to:
classify the R-S amplitude difference value into either the first state or the second state based on whether the R-S amplitude difference value exceeds a predetermined numerical threshold.

4. The computer system of claim 1, wherein one or more computer processors are further configured to:
filter the ECG signal using a median filter and a low-pass filter; and
control noise associated with the ECG signal based on filtering.

5. A computer-implemented method comprising:
measuring, by at least one computer processor, one or more instances of an electrocardiogram (ECG) signal categorized in sequentially input datasets, wherein each ECG signal is in either:
a first state in which the ECG signal is idle; or
a second state in which noise is generated;
extracting, by the at least one computer processor, one or more feature points of each measured ECG signal in the first state and in the second state, wherein extracted feature points comprise an R-peak value and an S-peak value of a respective ECG signal;
performing, by the at least one computer processor, K-means clustering on one or more instances the ECG signal in the first state or the second states based on extracted feature points and generating clustered ECG signals based on performed K-means clustering; and
classifying, by the at least one computer processor, stress experienced by a subject in the first state or the second state based on an R-peak value and an S-peak value calculated based on clustered ECG signals and training a long-short term memory (LTSM), a type of recurrent neural network (RNN), to recognize patterns in clustered ECG signals even when a distance between sequentially input datasets is relatively long.

6. The computer-implemented method of claim 5 further comprising:
determining, by the at least one computer processor, an R-S amplitude difference value based on classification of stress in the first state or the second state, wherein:
the R-S amplitude difference value is indicative of a difference between the R-peak value and the S-peak value and expresses ECG as stress levels compared with the R-S amplitude difference value.

7. The computer-implemented method of claim 6 further comprising:
classifying, by the at least one computer processor, the R-S amplitude difference value into either the first state or the second state based on whether the R-S amplitude difference value exceeds a predetermined numerical threshold.

8. The computer-implemented method of claim 5 further comprising:
   filtering, by the at least one computer processor, the ECG signal using a median filter and a low-pass filter; and
   controlling, by the at least one computer processor, noise associated with the ECG signal based on filtering.

9. A computer-readable recording medium having embedded therein a set of instructions which, when executed by one or more processors of a computer, causes the computer to execute operations comprising:
   measuring one or more instances of an electrocardiogram (ECG) signal categorized in sequentially input datasets, wherein each ECG signal is in either:
      a first state in which the ECG signal is idle; or
      a second state in which noise is generated;
   extracting one or more feature points of each measured ECG signal in the first state and in the second state, wherein extracted feature points comprise an R-peak value and an S-peak value of a respective ECG signal;
   performing K-means clustering on one or more instances the ECG signal in the first state or the second states based on extracted feature points and generating clustered ECG signals based on performed K-means clustering; and
   classifying stress experienced by a subject in the first state or the second state based on an R-peak value and an S-peak value calculated based on clustered ECG signals and training a long-short term memory (LTSM), a type of recurrent neural network (RNN), to recognize patterns in clustered ECG signals even when a distance between sequentially input datasets is relatively long.

10. The computer-readable recording medium of claim 9 further comprising:
   determining an R-S amplitude difference value based on classification of stress in the first state or the second state, wherein:
      the R-S amplitude difference value is indicative of a difference between the R-peak value and the S-peak value and expresses ECG as stress levels compared with the R-S amplitude difference value.

11. The computer-readable recording medium of claim 10 further comprising:
   classifying the R-S amplitude difference value into either the first state or the second state based on whether the R-S amplitude difference value exceeds a predetermined numerical threshold.

12. The computer-readable recording medium of claim 9 further comprising:
   filtering the ECG signal using a median filter and a low-pass filter; and
   controlling noise associated with the ECG signal based on filtering.

* * * * *